United States Patent
Wang et al.

(10) Patent No.: US 10,945,416 B2
(45) Date of Patent: *Mar. 16, 2021

(54) BAY SCALLOP X PERUVIAN SCALLOP HYBRID THREE-LINE BREEDING SYSTEM AND METHOD

(71) Applicants: Qingdao Agricultural University, Shandong (CN); Qingdao Oceanwide BioTech Co., Ltd., Shandong (CN)

(72) Inventors: Chunde Wang, Shandong (CN); Bin Ma, Shandong (CN); Kuifu Sun, Shandong (CN); Yuming Zhao, Shandong (CN); Bo Liu, Shandong (CN); Shun Zhou, Shandong (CN); Wenqi Wang, Shandong (CN); Xia Zhao, Shandong (CN); Guoying Miao, Shandong (CN)

(73) Assignees: QINGDAO AGRICULTURAL UNIVERSITY, Qingdao (CN); QINGDAO OCEANWIDE BIOTECH CO., LTD., Qingdao (CN)

( * ) Notice: Subject to any disclaimer, the term of this patent is extended or adjusted under 35 U.S.C. 154(b) by 333 days.

This patent is subject to a terminal disclaimer.

(21) Appl. No.: 15/310,319

(22) PCT Filed: Sep. 2, 2014

(86) PCT No.: PCT/CN2014/085719
§ 371 (c)(1),
(2) Date: Nov. 10, 2016

(87) PCT Pub. No.: WO2016/029490
PCT Pub. Date: Mar. 3, 2016

(65) Prior Publication Data
US 2017/0245477 A1 Aug. 31, 2017

(30) Foreign Application Priority Data
Aug. 27, 2014 (CN) .......................... 201410429453.6

(51) Int. Cl.
A01K 67/027 (2006.01)
A01K 67/00 (2006.01)
A01K 67/033 (2006.01)
A01K 61/54 (2017.01)

(52) U.S. Cl.
CPC ............ *A01K 61/54* (2017.01); *A01K 67/033* (2013.01); *Y02A 40/81* (2018.01)

(58) Field of Classification Search
CPC ....... A01K 67/00; A01K 61/54; A01K 67/033
USPC ......................................................... 800/20
See application file for complete search history.

(56) References Cited

FOREIGN PATENT DOCUMENTS

| | | |
|---|---|---|
| CN | 102217561 | 10/2011 |
| CN | 102308770 | 1/2012 |
| CN | 102318571 | 1/2012 |

OTHER PUBLICATIONS

ISR for PCT/CN2014/085719 completed Apr. 7, 2015.

*Primary Examiner* — Valarie E Bertoglio
(74) *Attorney, Agent, or Firm* — Guosheng Wang; United States Research and Patent Firm

(57) ABSTRACT

The current invent relates to the construction and application of a three-line breeding system in the bay scallop×Peruvian scallop hybrids. The said three-line consists of a male sterile line, a maintainer line and a restorer line. A combination of male sterile line and maintainer line is obtained by continuously backcrossing the male sterile individuals selected from $F_1$ inter-specific hybrid families with sperm of the selfing family of the sperm-providing Peruvian scallops until the progenies are all male sterile. The restorer line is obtained by continuously backcrossing selected individuals from the male sterile line with sperm of the selfing family of a Peruvian scallop until the progenies are all hermaphroditic and exhibit excellent production traits. Commercial male sterile brood stocks are produced by backcrossing the male sterile line with the maintainer line and commercial hybrid spats are produced by backcrossing the male sterile line and the restorer line.

2 Claims, No Drawings

BAY SCALLOP X PERUVIAN SCALLOP HYBRID THREE-LINE BREEDING SYSTEM AND METHOD

FIELD OF THE INVENTION

The present invention relates to a breeding method for commercial production of hybrid scallops, and in particular, relates to the construction and application of a three-line breeding system, comprising of a male sterile line, a maintainer line and a restorer line, in the bay scallop×Peruvian scallop hybrids.

BACKGROUND OF THE INVENTION

The bay scallops (*Argopecten irradian irradians*) are native to the U.S. Atlantic coasts and was first introduced into China in 1952. The bay scallops grow fast and adapt to a wide range of temperature with high tolerance to environmental stresses, and thus are very suitable for aquaculture in China seas. At present, the bay scallop accounts for more than 50% of the total production of cultured scallops in northern China. However, due to long-term inbreeding after its original introduction, the genetic quality of the bay scallops has heavily degraded, as manifested by its ever-decreasing body size and relatively high mortality rates. Hence, the scallop aquaculture industry has an urgent need for scallops tocks with improved performance especially in grow and survival.

To find a better scallop stock for the sustainable scallop culture industry in China, the inventors introduced the Peruvian scallops (*Argopecten purpuratus*) into China from Peru for the first time in 2007. The Peruvian scallops, which belong to the same genus *Argopecten* as the bay scallops, are fast-growing, medium-sized scallops native to the South Pacific coasts. The two species of *Argopecten* scallops are similar in that both are hermaphroditic scallops with same chromosome number and similar karyotypes, and are thus possible to hybridize with each other. Unlike the bay scallops, culture of the Peruvian scallops in China was not successful as they could not survive the high temperature in the summer or low temperature in the winter. To utilize the genetic resources of the two *Argopecten* scallops, the inventors carried out the interspecific hybridization between the bay scallops and the Peruvian scallops and produced the $F_1$ bay scallop×Peruvian scallop hybrids with superior performance especially in growth (Wang et al., 2011). The $F_1$ hybrids exhibited extraordinary high heterosis in growth in that their whole body weight was increased by 97.5% in the *A. i. irradians×A. purpuratus* cohorts compared with that of the bay scallops in the first year. In addition, unlike the bay scallops which normally die in the following spring after spawning, the $F_1$ hybrids could survive the summer and whiter in China seas and grow to a whole body weight of up to 200 g in the following year (Chunde Wang et al., 2009. Study on interspecific hybridization of Peruvian scallops and bay scallops. Marine Sciences, 33(10): 84-87; Chunde Wang et al., 2011. Introduction of the Peruvian scallop and its hybridization with the bay scallop in China, Aquaculture, 2011, 310:380-387).

Despite their high hybrid vigor, the bay scallop×Peruvian scallop hybrids are hard to produce at large scales as both parent stocks are hermaphrodites which release sperm and eggs simultaneously during spawning. The released eggs are prone to being fertilized by sperm of the same scallop or from other animals of the same species, making it hard to collect unfertilized eggs for inter-specific hybridization. This greatly reduces the percentage of real hybrid progenies in the commercial spat batches and also the magnitude of the overall increases in growth of the progenies.

Studies have shown that the hermaphroditic characteristic of the two *Argopecten* scallops is similar to the monoecious characteristic of many agricultural crops. Normally, artificial emasculation is required to solve the problem of same-flower pollination in the breeding of the monoecious crops. Similar situation also exists in the hybridization between the bay scallop and the Peruvian scallop. In agriculture, the key to solve the problem of same-flower pollination depends on the discovery of male sterile (and yet female fertile) plants. A three-line breeding system, comprising of the male sterile line, maintainer line and the restorer line can then be obtained by continuously backcrossing the male sterile plant with pollen from an inbreeding line and can be used to produce pure hybrids at commercial scales. So far, the three-line breeding systems have been established in hundreds of agricultural crops around the world and are widely applied in the commercial production of hybrid plants in agriculture.

Up to now, in animal breeding, no male sterile and yet female fertile animals have been found and as a result, no similar three-line breeding system has been established for production of hybrids in animals so far. Obviously, establishment of such three-line breeding systems is essential for the production of inter-specific hybrids between hermaphroditic scallops at large scales and low costs, and represents a major breakthrough in animal breeding technology.

SUMMARY OF THE INVENTION

One object of the present invention is to overcome the deficiency of the existing hybrid scallop breeding technology by establishing a three-line breeding system.

Another object of the present invention is to establish application method of such three-line breeding system for the efficient production of hybrid seeds from two hermaphroditic scallops, such as the bay scallop and the Peruvian scallop, at large scales and low costs.

The three lines herein refer to the male sterile line, the maintainer line and the restorer line of the scallops. The male sterile line is a line that produces fertilizable eggs, but no functional sperm and is capable of transmitting its male sterile characteristic to its progenies. It is obvious that the male sterile line is the core line in the three-line system and plays a key role in providing a large number of unfertilized eggs in commercial production of the hybrid seeds. The reproduction of the male sterile line depends on its corresponding maintainer line. The male sterile line is obtained by continuously backcrossing the accidentally discovered male-sterile but yet female-fertile individuals in the $F_1$ hybrids with the selling family of their male parents (sperm-providing scallops) to construct backcross families until all the individuals in the backcross families are male sterile and yet female fertile.

A maintainer line is specific for a certain male sterile line; when the maintainer line is hybridized with the male sterile line, the resulted first filial generation will keep the male sterile characteristic; the major function of the maintainer line is to provide sperms necessary for breeding the male sterile line. The maintainer line is selected together with its corresponding male sterile line. In selecting the male sterile line and its maintainer line, the eggs of the male-sterile but yet female-fertile individuals in the $F_1$ hybrids are fertilized with sperm of the selfing family of their male parent (sperm-providing Peruvian scallop) to construct backcross families. In the following year, the male- and female fertility of the backcross families are tested. The backcross family that is male-sterile and yet female-fertile becomes the male sterile line and the selfing family of the male parent (sperm-providing Peruvian scallop) becomes the maintainer line specific for this male-sterile line. In this invention, the maintainer line is a hermaphroditic Peruvian scallop selfing family that is capable of breeding the next-generation maintainer line through self-fertilization.

The restorer line is also known as the restorer line for a male sterile line. The progenies produced from the eggs of the male sterile line and the sperm of the restorer line are hermaphroditic, i.e., both female- and male-fertile. Hence, the role of the restorer line is to provide sperm that are used to fertilize eggs from the male sterile line to produce hybrid seeds in commercial operations. The restorer line is a Peruvian scallop line obtained by continuously backcrossing the sperm of Peruvian scallops with the eggs of the male sterile line until all the backcrossed progenies are hermaphrodites. The restorer line is reproduced by self-fertilization.

The present invention is based on the following ideas and facts: 1) The inventors have discovered in their previous studies that the F1 Bay scallop×Peruvian scallop hybrids that produced with the eggs of the Bay scallops and the sperm of the Peruvian scallops contain 2-10% of male sterile individuals in the *A. i. irradians*×*A. purpuratus* cohort that produce only fertile eggs but not fertile sperm. The eggs from these $F_1$ hybrids can be fertilized by sperm from the Peruvian scallops and the resulted fertilized eggs can develop normally to produce backcrossed families. Most backcrossed hybrids exhibited excellent production traits in growth rate and temperature tolerance. Compared with the Bay scallops produced at the same time and cultured under same conditions, the average whole body weight of the best backcrossed cohorts was more than 100% higher; 2) Studies also showed that 8-10% individuals in the above backcrossed hybrids are still male sterile and yet female fertile. Thus, it is possible to obtain a combination of a male sterile line (serving as the female parent) and a Peruvian scallop selfing line (serving as the male parent) whose hybridized progenies are still male sterile and female fertile, by continuously backcrossing the eggs from the male sterile line with the sperm of the Peruvian scallop line for a couple of generations. This Peruvian scallop line in the above combination is capable of conferring the male sterile characteristic to the progenies of the male sterile line and is thus referred to as the maintainer line for that specific male sterile line; 3) It has been further discovered that about 90% of the backcrossed hybrids produced from the eggs of the male sterile individuals fertilized with the sperm from the Peruvian scallops were hermaphroditic. Thus it is possible to obtain a combination of a male sterile line (serving as the female parent) and a Peruvian scallop selfing line (serving as the male parent) whose hybridized progenies are all hermaphrodites that produce both fertile eggs and sperm, by continuously backcrossing the sperm of the Peruvian scallop line with the eggs from the male sterile line for a couple of generations. This Peruvian scallop line in the above combination is capable of restoring the male fertility in their progenies with the male sterile line and is thus referred to as the restorer line for that specific male sterile line; 4) In commercial operations, the male sterile (and yet female fertile) brood stocks can be produced at large scales by fertilizing the eggs from the male sterile line with sperm from the maintainer line and commercial hybrid seeds with excellent performance can be produced by fertilizing the eggs of the male sterile stocks with the sperm of the corresponding restorer line at large scales and low costs.

The establishment method of the male sterile line, maintainer line and the restorer line of the bay scallop×Peruvian scallop hybrids of the present invention is as follows:

1) Production of the Male Sterile Individuals in the Scallop× Peruvian Scallop Hybrids and Breeding of the Male Parents Thereof:

Large bay scallop and Peruvian scallop brood stocks are conditioned for maturation synchronously. They are then induced to spawn in individual containers at the same time under close observation by routine air exposure and thermal shock as used in the spawning induction of the bay scallops. The eggs of the bay scallops and the Peruvian scallops are collected, if no sperm release is observed and set aside for 20 min when they are checked under a microscope to make sure no fertilized eggs are present. The sperm of the Peruvian scallops are collected by filtering the seawater containing the sperm through a 500-mesh screen (with a diameter of 25 μm) to remove eggs, if any. Then, the $F_1$ bay scallop× Peruvian scallop hybrids are produced by mixing the eggs of the bay scallop with an appropriate amount of sperm from the Peruvian scallop. Meanwhile, the eggs of the Peruvian scallop which provides sperm in the above $F_1$ hybrid are fertilized with its own sperm to make a selfing family for this Peruvian scallop. Due to the very low ratio of the male sterile individuals in the $F_1$ hybrids, a large number of $F_1$ hybrid families need to be established in order to find male sterile individuals for breeding the male sterile line as described below.

2) Breeding of the Male Sterile Line and the Maintainer Line:

In the following year, $F_1$ hybrids are conditioned to mature and induced to spawn. Individuals spawn only eggs and the eggs can be fertilized by sperm from Peruvian scallops are considered as male sterile individuals and chosen for further selection of male sterile line. Meanwhile, large individuals from the selfing family of sperm-providing Peruvian scallop, of $F_1$ hybrids are also conditioned to mature. Both the selected male sterile scallops and the Peruvian scallops from the setting family are induced to spawn at the same time. The spawned eggs of the male sterile scallops are fertilized with sperm of the Peruvian scallop selected from the selfing family to construct backcross families. The next generation selfing family of the sperm-providing Peruvian scallop is also produced by fertilizing its own eggs and sperm.

In the subsequent years, male sterile individuals are again selected from the backcross families from previous year and conditioned to ripeness. The eggs from these male sterile individuals are fertilized with sperm from large individuals selected from the Peruvian scallop selfing family which are again reproduced by self-fertilization. Such backcross breeding is carried out continuously until all the backcross progenies are male sterile and yet female fertile. At this point, the backcross progenies become the male sterile line while the Peruvian scallop selfing family becomes the corresponding maintainer line. In commercial practices, the male sterile line brood stocks are reproduced by fertilizing the eggs from the scallops of the male sterile line with the sperm of the Peruvian scallops of the maintainer line, and the maintainer line brood stocks are reproduced by self-fertilization.

3) Breeding of the Restorer Line:

After the male sterile line and its corresponding maintainer line combination is obtained, excellent male sterile individuals from the male sterile line are selected and conditioned to mature. After Spawning induction, the eggs from a male sterile individual are fertilized with sperm from different Peruvian scallops to construct backcross families. The eggs front this male sterile individual are mixed with sperm from its corresponding maintainer line to produce the next generation male sterile line. The sperm-providing Peruvian scallop is also reproduced by self-fertilization. During the adult grow-out stage, the growth and survival rates of the hybrid progenies are measured and combining ability tests are carried out.

In the following year, excellent individuals are selected from both the male sterile line and the corresponding sperm-providing Peruvian scallop selfing family that correlated to the best backcross family with the highest growth and survival rate and highest percentage of hermaphroditic individuals and conditioned to mature. After spawning induction, the eggs from the male sterile individual are again fertilized with sperm of the selected Peruvian scallops to produce next generation backcross families. Same selection is repeated each year until the backcross families are all hermaphroditic and excellent in production traits. The Peruvian scallop selfing family that can render male fertility to the progenies of the male sterile line becomes the restorer line. The restorer line can be reproduced by self-fertilization as they are hermaphrodites. In commercial operations, the restorer line is used to provide sperm that can be mixed with eggs from the male sterile line to produce commercial hybrid spats at large scales and low costs.

5) Reproduction of the Male Sterile Line, the Maintainer Line and the Restorer Line:

This invention also establishes the methods for the reproduction of the male sterile line, the maintainer line and the restorer line. The next generation male sterile line is reproduced by fertilizing the eggs from the male sterile line with sperm from its corresponding maintainer line. The next generation maintainer line and the restorer line are reproduced by self-fertilization, i.e., fertilization of eggs with their own sperm, as both lines are hermaphroditic Peruvian scallops.

6) Production of Commercial Hybrid Spats Using the Three-Line Breeding System:

The brood stocks of the male sterile line and the restorer line are selected in the ratio of 5:1. After the scallops are conditioned to ripeness using the conventional methods, the brood stocks of the male sterile line are induced to spawn eggs and the scallops of the restorer line are induced to spawn eggs and sperm. Then seawater containing the sperm-eggs mixture of the restorer line is filtered using a 500-mesh screen (with a diameter of 25 μm) to collect sperm of the restorer line, which is added to the spawning tank of the male sterile line and stirred. Seawater samples from the spawning tanks are frequently checked under a microscope until each egg is surrounded by 5-6 sperm. Commercial hybrid spats are obtained after the fertilized eggs hatch.

The present invention can be used in the construction and application of similar three-line breeding system between all hermaphroditic *Argopecten* scallops including, but not limited to *Argopecten irradians irradians, A. irradians concentricus, A. purpuratus, A. gibbus*, and *A. ventricosus*, etc. Furthermore, the methods outlined in this invention can also be used in other hermaphroditic scallops such as the Pecten scallops and even in other hermaphroditic invertebrates.

The three-line breeding system of the bay scallop×Peruvian scallop hybrids established in this invention is the first three-line breeding system established in the scallops and also in the animal kingdom, representing a major breakthrough in the animal breeding technology. The present invention effectively overcomes the barrier of self-fertilization in the hybridization process of the hermaphroditic scallops and enables complete hybridization at large scales and low costs. Therefore, the hybrid vigor can be fully utilized in the hybrid progenies which possess the advantages of both scallops in terms of growth, body size and temperature tolerance, etc. Hence, the bay scallop×Peruvian scallop hybrids can be successfully cultured in northern China seas such as Qingdao and Dalian, with an increase in yield by over 50% in the first year compared with the bay scallops.

DETAILED DESCRIPTION OF THE EMBODIMENTS

The present invention establishes a three-line breeding system, comprising of a male sterile line, a maintainer line and a restorer line of bay scallop×Peruvian scallop hybrids and also application methods for commercial production of the bay scallop×Peruvian scallop hybrid spats using the three-line breeding system. The specific steps are as follows:

Embodiment 1

1) Production of the Male Sterile Individuals of the Bay Scallop×Peruvian Scallop Hybrids and Reproduction of the Sperm-Providing Peruvian Scallops:

In the first year, 50 bay scallops and 50 Peruvian scallops with mature gonads are selected. Alter air exposure for 30 min., scallops are placed in separate containers pre-filled with 23° C. seawater for spawning induction. After spawning, the eggs and sperm of each scallop are collected separately. Eggs of a bay scallop are mixed with sperm of a Peruvian scallop to produce a bay scallop×Peruvian scallop $F_1$ hybrid family. A selfing family is produced for each sperm-providing Peruvian scallop by mixing its eggs with its own sperm. In all cases, only a small amount of sperm are used to avoid adverse effect caused by excess sperm. Ideally, each egg should be surrounded by 5-6 sperm. The fertilized eggs are hatched in dark and the resulted D-larvae are collected. At least 20 $F_1$ hybrid families and the corresponding selfing family of the sperm-providing Peruvian scallop are established. Larval culture, spat nursery and adult grow-out are carried out following the routine culture methods for the bay scallops.

2) Breeding of the Male Sterile Line of the Bay Scallop×Peruvian Scallop Hybrids:

In the next spring, at least 100 individuals with excellent production traits and apparent male sterile gonad (with no obvious gonadal development in the male part of the gonad) are selected from each $F_1$ hybrid family. Twenty scallops with excellent production traits are also selected from each selfing families of the corresponding sperm-providing Peruvian scallops. After conditioning, test spawning is carried out to determine if the individuals selected from the $F_1$ hybrid families spawn only eggs and the eggs can be fertilized and thus to select the male sterile and yet female fertile $F_1$ hybrid families. Then at least 50 backcross families are constructed with the eggs from selected male sterile/female fertile individuals and sperm from selected individuals from the corresponding selfing families of the sperm-providing Peruvian scallop. The sperm-providing Peruvian scallop brood stocks of the backcross families are again reproduced by self-fertilization. In the following years, the male sterile/female fertile individuals from the backcross families are continuously backcrossed with individuals selected from the selfing family of the sperm-providing Peruvian scallops, until all the individuals of the backcross progenies exhibit excellent traits and are male sterile and female fertile. The male sterile line of the bay scallop×Peruvian scallop hybrids is thus obtained and the selfing family of the sperm-providing Peruvian scallop becomes the corresponding maintainer line for this male sterile line.

3) Breeding of the Maintainer Line of the Bay Scallop×Peruvian Scallop Hybrids:

Individuals with excellent production traits are selected from the maintainer line and conditioned to mature. As the scallops of the maintainer line are hermaphroditic animals, the maintainer line is reproduced by self-fertilization.

4) Breeding of the Restorer Line of the Bay Scallop×Peruvian Scallop Hybrids:

Fifty large male sterile and female fertile individuals are selected from the male sterile line and the maintainer line respectively and conditioned to ripeness. They are then induced to spawn and the eggs from the male sterile individuals are fertilized by the sperm of different Peruvian scallops to establish at least 20 backcross families; meanwhile, the sperm-providing Peruvian scallops are self-fertilized to establish the corresponding self-fertilization families. At harvest, the growth and survival rates of the backcross progenies are measured and the combining ability tests are carried out for each backcross family. In the following year, excellent individuals are selected from both the male sterile line and the corresponding sperm-providing Peruvian scallop selfing family that correlated to the best backcross family with the highest combining ability and highest percentage of hermaphroditic individuals. After conditioning and spawning induction, eggs from the male sterile line are again backcrossed with the sperm of the selected individual from the selfing family of the sperm-providing Peruvian scallop. Same selections are carried each year on the selfing family of the sperm-providing Peruvian scallop until all individuals in the backcross family are hermaphroditic and exhibit excellent production traits. This selfing family of the sperm-providing Peruvian scallop becomes the restorer line for the corresponding male sterile line. The hermaphroditic restorer line is reproduced by self-fertilization and provides sperm for the commercial production of hybrid spats.

5) Production of Commercial Bay Scallop×Peruvian Scallop Hybrid Spats Using the Three-Line Breeding System:

Each year, the brood stocks of the male sterile line are produced by hybridizing the male sterile line with the sperm of its maintainer line while the brood stocks of the restorer line are reproduced by self-fertilization. In commercial scallop hatcheries, the brood stocks of the male sterile line and the restorer line are selected in the ratio of 5:1 and conditioned to ripeness at the same time. Then the brood stocks of the male sterile line are induced to spawn in large tanks and the brood stocks of the restorer line are induced to spawn in 20 liter buckets. The sperm of the restorer line are collected by filtering the seawater in the buckets through a 500-mesh screen and added to the spawning tanks containing the eggs from the male sterile line brood stocks and well stirred immediately. Seawater samples are taken frequently from the tanks for observation of the fertilization under a microscope until 5-6 sperm are found around each egg. The commercial bay scallop-Peruvian scallop hybrid seeds can thus be produced at large scales and low costs.

Embodiment 2

In late March 2008, mature bay scallops and Peruvian scallops were selected and induced to spawn in separate Jars under close observation. The eggs of the bay scallops that did not spawn sperm were collected and fertilized with mixed sperm of different Peruvian scallops to produce $F_1$ bay scallop×Peruvian scallop hybrid spats. In spring 2009, the scallops of the above $F_1$ hybrids were conditioned to ripeness and those large scallops With only female part of the gonad developed were selected. The selected $F_1$ scallops were induced to spawn by air exposure for 30 min followed by thermal shock in jars pre-filled with 23° C. seawater. The eggs of the bay scallop×Peruvian scallop hybrids were then fertilized with sperm of Peruvian scallops to construct the first-filial generation of backcross cohorts of the bay scallop-Peruvian scallop hybrids (BCC). In spring 2010, after conditioning in the hatchery, it was found that in the $BC_1$ cohort, most individuals were hermaphroditic while less than 10% of the individuals were male sterile.

These male sterile scallops can be continuously backcrossed with the sperm of the self-fertilized progenies of the sperm-providing Peruvian scallops. After one to several generations of selective breeding, a combination of a male sterile line (serving as the female parent)-maintainer line (serving as the male parent) can be obtained whose hybridized progenies will be all male sterile and yet female fertile. In commercial operations, the male sterile brood stocks can be produced by fertilizing the eggs from the male sterile line with the sperm from the maintainer line at large scales and low costs.

Once the combination of male sterile line and its maintainer line is established, the restorer line of the male sterile line can be selected in the following way. Large individuals in the male sterile line are selected for conditioning and induced to spawn unfertilized eggs. These eggs are fertilized by the sperm of different, unrelated Peruvian scallops to establish least 20 backcross families. The families containing highest percentage of hermaphroditic animals and exhibit superior production traits based on combining ability tests are selected. In the following years, the selfing families of the Peruvian scallops corresponding to the selected backcross families are continuously selected by backcrossing with the male sterile line until all individuals in the resulted backcross families are hermaphrodites and perform excellently in major production traits. The selfing family of the Peruvian scallops then becomes the restorer line for the corresponding male sterile line and can be used together with the male sterile line to produce commercial hybrid spats at large scales and low costs in commercial scallop hatcheries.

Embodiment 3

In spring 2010, the male sterile individuals in the $F_1$ bay scallop×Peruvian scallop hybrids established in 2009 were selected, conditioned to ripeness and induced to spawn. The eggs from the male sterile individuals in the bay scallop×Peruvian scallop hybrid population were fertilized with sperm of the Peruvian scallops to establish 8 backcross families. In the spring of 2011, it was discovered that, after the scallops were conditioned to ripeness, in all backcross families, most individuals were hermaphroditic, suggesting that it is possible to breed the restorer line by backcrossing the Peruvian scallops with the male sterile individuals selected from the $F_1$ bay scallop×Peruvian scallop hybrids.

Embodiment 4

In 2012, two (bay scallop×Peruvian scallop)×Peruvian scallop backcross families were constructed with eggs from $F_1$ bay scallop×Peruvian scallop hybrids and sperm from Peruvian scallops. At harvest in mid-November 2012, the average shell height, average shell length, average shell width and the average whole weight were increased by 46.3%, 45.7%, 32.3% and 134.9% in one backcross family, and by 28.2%, 29.5%, 16.4% and 74.0% in another backcross family, respectively, compared with the bay scallops produced and cultured under same conditions and over the same period. The results showed that the backcross family exhibited great production traits in growth.

After maturation in the spring of 2013, it was discovered that the progenies of one (bay scallop×Peruvian scallop)× Peruvian scallop backcross families were all hermaphrodites, indicating again that the restorer line of the male sterile line can be successfully bred by backcrossing the Peruvian scallops with the male sterile individuals. In most progenies in another (bay scallop×Peruvian scallop)×Peruvian scallop family backcross family, only the female part of their gonads developed and furthermore, the spawned eggs can be fertilized by Peruvian scallops sperm, suggesting that it is possible to breed the male sterile line and the maintainer line by continuously backcrossing the Peruvian scallops with the male sterile individuals.

Embodiment 5

In 2013 and 2014, 12 $F_1$ bay scallop×Peruvian scallop hybrid families together with the selfing families of their sperm-providing Peruvian scallops were established. According to the methods given in Embodiment 1, the male sterile families of the bay scallop-Peruvian scallop hybrids and the corresponding maintainer line and restorer line thereof can be bred and the production of commercial bay scallop-Peruvian scallop hybrid spats can be realized within 1-3 years.

What is claimed is:

1. A three-line breeding system using Bay scallop×Peruvian scallop hybrids, the system comprising:
   a male sterile line, comprising a Bay scallop×Peruvian scallop hybrid line that is male-sterile and yet female-fertile and spawns only eggs;
   a maintainer line, comprising a Peruvian scallop line that provides speitn to fertilize eggs of the male-sterile line to produce a next generation male-sterile line; and
   a restorer line, comprising a Peruvian scallop line that provides sperm to fertilize eggs of the male-sterile line to produce commercial hermaphroditic hybrid scallops.

2. A three-line breeding method using Bay scallop× Peruvian scallop hybrids, the method comprising:
   1) selecting $F_1$ male-sterile individuals from $F_1$ Bay scallop×Peruvian scallop hybrid families and also Peruvian scallop individuals from the corresponding selfing Peruvian scallop family, comprising:
   1a) producing, for step 1b, $F_1$ hybrid families wherein each family is produced using eggs from a Bay scallop and sperm from a Peruvian scallop, meanwhile each Peruvian scallop that provides sperm is used to produce a corresponding selfing Peruvian scallop family for step 1c,
   1b) selecting, for step 2a, male-sterile individuals from the $F_1$ hybrid families produced in step 1a, wherein the individual is determined to be male-sterile if it only spawns eggs; and
   1c) selecting, for step 2a, Peruvian scallop individuals from each corresponding selfing Peruvian scallop family produced in step 1a;
   2) breeding a male-sterile line, comprising:
   2a) Producing, for step 2b backcross families wherein each backcross family is produced using eggs from a selected male-sterile $F_1$ hybrid individual produced in step 1b and sperm from the corresponding selected Peruvian scallop individual selected to step 1c, meanwhile each Peruvian scallop that provides sperm is used to produce a corresponding selfing Peruvian scallop family for step 2b and step 2d;
   2b) selecting from the backcross families produced in step 2a, for step 2c, a backcross family wherein each individual in this family is male-sterile/female-fertile, wherein the individual is determined to be male-sterile/female-fertile if it spawns only eggs and the spawned eggs can be fertilized by sperm of the selected Peruvian scallop individuals from the corresponding selfing Peruvian scallop family produced in step 2a and produce progenies;
   2c) obtaining male-sterile line, wherein the backcross family produced in step 2b is selected as the male-sterile line; and
   2d) selecting, for step 3, the selfing Peruvian scallop family corresponding to the male-sterile line selected in step 2c;
   3) obtaining a maintainer line from step 2d, wherein the selfing Peruvian scallop family selected in step 2d is selected as the maintainer line specific for the male-sterile line produced in step 2c, as this selfing Peruvian scallop family is able to render the male-sterile/female-fertile characteristics to the progenies of the male-sterile line produced in step 2c,
   4) breeding a restorer line, comprising:
   4a) producing, for step 4b, hybrid families using eggs from individuals of the male-sterile line produced in step 2c and sperm of Peruvian scallops that are not genetically related to the male-sterile line produced in step 2c, meanwhile each Peruvian scallop that provides sperm is used to produce a corresponding selfing family for step 4c,
   4b) selecting, from the hybrid families produced in step 4a, a hybrid family wherein each individual in this hybrid family is hermaphroditic; and
   4c) selecting a restorer line, which is the selfing Peruvian scallop family produced in step 4a corresponding to the hybrid family selected in step 4b, as this selfing Peruvian scallop family is able to restore the male-fertility of the progenies of the male sterile line produced in step 2c; and
   5) reproducing the three-line breeding system, wherein a next generation of male-sterile line is produced by fertilizing the eggs of the male-sterile line produced in step 2c with the sperm from the corresponding maintainer line produced in step 3, and the commercial hermaphroditic hybrid scallops are produced by fertilizing the eggs of the male-sterile line produced in step 2c with the sperm from the corresponding restorer line produced in step 4c.

* * * * *